US008410124B2

(12) United States Patent
Masse

(10) Patent No.: US 8,410,124 B2
(45) Date of Patent: Apr. 2, 2013

(54) DEUTERATED ETRAVIRINE

(75) Inventor: Craig E. Masse, Cambridge, MA (US)

(73) Assignee: Concert Pharmaceuticals Inc., Lexington, MA (US)

( * ) Notice: Subject to any disclaimer, the term of this patent is extended or adjusted under 35 U.S.C. 154(b) by 947 days.

(21) Appl. No.: 12/288,186

(22) Filed: Oct. 17, 2008

(65) Prior Publication Data
US 2009/0105147 A1 Apr. 23, 2009

Related U.S. Application Data

(60) Provisional application No. 60/980,869, filed on Oct. 18, 2007.

(51) Int. Cl.
A61K 31/505 (2006.01)
C07D 239/02 (2006.01)
(52) U.S. Cl. ..................... 514/272; 544/321
(58) Field of Classification Search .................. 514/272; 544/321
See application file for complete search history.

(56) References Cited

U.S. PATENT DOCUMENTS

| 5,304,121 | A | 4/1994 | Sahatjian |
| 5,886,026 | A | 3/1999 | Hunter et al. |
| 6,099,562 | A | 8/2000 | Ding et al. |
| 6,221,335 | B1 | 4/2001 | Foster |
| 6,440,710 | B1 | 8/2002 | Keinan et al. |
| 6,603,008 | B1 | 8/2003 | Ando et al. |
| 6,803,031 | B2 | 10/2004 | Rabinowitz et al. |
| 7,014,866 | B2 | 3/2006 | Infeld et al. |
| 7,241,458 | B1 | 7/2007 | Verreck et al. |
| 7,517,990 | B2 | 4/2009 | Ito et al. |
| 2006/0079502 | A1 | 4/2006 | Lang |
| 2006/0094744 | A1 | 5/2006 | Maryanoff et al. |
| 2007/0082929 | A1 | 4/2007 | Gant et al. |
| 2007/0197695 | A1 | 8/2007 | Potyen et al. |
| 2008/0103122 | A1 | 5/2008 | Veltri |

FOREIGN PATENT DOCUMENTS

| CN | 1 687 060 | 4/2005 |
| EP | 1 002 795 | 3/2003 |
| WO | 95/26325 | * 3/1995 |
| WO | WO95/26325 | 10/1995 |
| WO | WO 00/27825 | 5/2000 |
| WO | WO 01/22938 | 4/2001 |
| WO | WO 2006/052373 | 5/2006 |
| WO | WO 2007/118651 | 10/2007 |

OTHER PUBLICATIONS (Kushner et al.,) Pharmacological Uses and Perspectives of Heavy Water and Deuterated Compounds; Canadian Journal of Physiology and Pharmacology; Feb. 1999, 77, 2; pp. 79-88.*
Andries et al., "TMC125, a novel next-generation nonnucleoside reverse transcriptase inhibitor active against nonnucleoside reverse transcriptase inhibitor-resistant human immunodeficiency virus type 1," *Antimicrob. Agents Chemother.*, 2004, 48(12):4680-4686.
Eichinger et al., "Stable Negative-Ion Isomers in the Gas Phase. $C_7H_7O$ Species," *Aust. J. Chem.*, 1989, 42:865-874.
Fisher et al., "The Complexities Inherent in Attempts to Decrease Drug Clearance by Blocking Sites of CYP-mediated Metabolism," *Curr. Opin. Drug Discovery Development*, 2006, 9(1):101-109.
Freireich et al., "Quantitative comparison of toxicity of anticancer agents in mouse, rat, hamster, dog, monkey, and man," *Cancer Chemother. Rep.*, 1966, 50(4):219-244.
Gannes et al., "Natural abundance variations in stable isotopes and their potential uses in animal physiological ecology," *Comp. Biochem. Physiol.*, 1998, 119A(3):725-737.
Gruzdev et al., "TMC125 is a highly potent non-nucleoside reverse transcriptase inhibitor (NNRTI) in antiretroviral therapy (ART)-Naïve, HIV-1 infected subjects," *41st Interscience Conference on Antimicrobial Agents and Chemotherapy*, 2001, Chicago, Abstract No. 1-668.
Houston and Carlile, "Prediction of hepatic clearance from microsomes, hepatocytes, and liver slices," *Drug Metab. Rev.*, 1997, 29(4):891-922.
Houston, "Utility of in vitro drug metabolism data in predicting in vivo metabolic clearance," *Biochem. Pharmacol.*, 1994, 47(9):1469-1479.
Isentress (raltegravir) Tablets, Oct. 2007, Merck & Co., 18-page product brochure.
Iwatsubo et al., "Prediction of in vivo drug metabolism in the human liver from in vitro metabolism data," *Pharmacol. Ther.*, 1997, 73(2):147-171.
Kushner et al., "Pharmacological Uses and Perspectives of Heavy Water and Deuterated Compounds," *Can. J. Physiol. Pharmacol.*, 1999, 77:79-88.
Lavé et al., "The use of human hepatocytes to select compounds based on their expected hepatic extraction ratios in humans," *Pharm. Res.*, 1997, 14(2):152-155.
Lazzarin et al., "Efficacy and safety of TMC125(etravirine) in treatment-experienced HIV-1-infected patients in DUET-2: 24-week results from a randomised, double-blind, placebo-controlled trial," *Lancet*, 2007, 370:39-48.
Lehnert et al., "Ortho-Methylation of Phenols with Ethyl(Iodomethyl)Zinc," *Tet. Lett.*, 1989, 30(39):5215-5218.
Littke et al., "Mild and general methods for the palladium-catalyzed cyanation of aryl and heteroaryl chlorides," *Org. Lett.*, 2007, 9(9):1711-1714.
Ludovici et al, "Evolution of anti-HIV drug candidates. Part 3: Diarylpyrimidine (DAPY) analogues," *Biorg. Med. Chem. Lett.*, 2001, 11:2235-2239.
Obach, "Prediction of human clearance of twenty-nine drugs from hepatic microsomal intrinsic clearance data: An examination of in vitro half-life approach and nonspecific binding to microsomes," *Drug Metab. Disp.*, 1999, 27(11):1350-1359.
Paul et al., "Regioselective Bromination of Activated Aromatic Substrates with N-Bromosuccinimide over HZSM-5," *Tet. Lett.*, 1994, 35(38):7055-7056.

(Continued)

Primary Examiner — James O Wilson
Assistant Examiner — Ebenezer O Sackey
(74) Attorney, Agent, or Firm — Fish & Richardson P.C.

(57) ABSTRACT

This disclosure relates to novel di-aryl-pyrimidine (DAPY) compounds and pharmaceutically acceptable salts thereof. This disclosure also provides compositions comprising a compound of this disclosure and the use of such compositions in methods of treating diseases and conditions that are beneficially treated by administering a non-nucleoside reverse transcriptase inhibitor (NNRTI).

15 Claims, No Drawings

OTHER PUBLICATIONS

Piscitelli et al., "TMC125 Does Not Alter Lopinavir/Ritonavir(LPV/RTV) Pharmacokinetics in Healthy Volunteers," *42nd Interscience Conference on Antimicrobial Agents and Chemotherapy*, 2002, San Diego, Abst. A-1824.

Raoof et al., "In Vivo Metabolism and Mass Balance of the Anti-HIV Compound TMC125 in Laboratory Animals and Healthy Volunteers," *AAPS J.*, 2006, 8(suppl 1):Abst. M1342.

Scientific Tables, 1970, *Geigy Pharmaceuticals*, Ardsley, N.Y., p. 537-538.

Suehiro et al., "Decay Reactions of Aryldiazenyl Radicals in Solution," *Bull. Chem. Soc. Jap.*, 1987, 60:3321-3330.

Wada and Hanba, "Natural abundance of carbon, nitrogen, and hydrogen isotope ratios in biogenic substances: present and future," *Seikagaku*, 1994, 66:15-30.

De Spiegeleer et al., "Synthesis and HPLC-purification of [$^{77}$Br]TMC125-R165335 (etravirine), a new anti-HIV drug of the DAPY-NNRTI class," *J. Label. Compd. Radiopharm.*, 2006, 49:683-686.

Foster, "Deuterium Isotope Effects in the Metabolism of Drugs and Xenobiotics: Implications for Drug Design," *Adv. Drug Res.*, 1985, 14:2-40.

Foster, "Deuterium isotope effects in studies of drug metabolism," *Trends in Pharmaceutical Sciences*, 1984, pp. 524-527.

Dyck et al., "Effects of Deuterium Substitution on the Catabolism of β-Phenylethylamine: An In Vivo Study," *J. Neurochem.*, 1986, 46:399-404.

Tonn et al., "Simultaneous Analysis of Diphenhydramine and a Stable Isotope Analog ($^2$H$_{10}$)Diphenhydramine Using Capillary Gas Chromatography with Mass Selective Detection in Biological Fluids from Chronically Instrumented Pregnant Ewes," *Biol. Mass Spectrometry*, 1993, 22:633-642.

Haskins, "The Application of Stable Isotopes in Biomedical Research," *Biomed. Mass Spectrometry*, 1982, 9(7):269-277.

Wolen, "The Application of Stable Isotopes to Studies of Drug Bioavailability and Bioequivalence," *J. Clin. Pharmacol.*, 1986, 26:419-424.

Browne, "Stable Isotope Techniques in Early Drug Development: An Economic Evaluation," *J. Clin. Pharmacol.*, 1998, 38:213-220.

Baillie, "The Use of Stable Isotopes in Pharmacological Research," *Pharmacol. Rev.*, 1981, 33(2):81-132.

Gouyette, "Synthesis of Deuterium-labelled Elliptinium and its Use in metabolic Studies," *Biomed Environ Mass Spectrometry*, 1988, 15:243-247.

Cherrah et al., "Study of Deuterium Isotope Effects on Protein Binding by Gas Chromatography/Mass Spectrometry. Caffeine and Deuterated Isotopomers," *Biomed Environ Mass Spectrometry*, 1987, 14:653-657.

Pieniaszek et al., "Moricizine Bioavailability via Simultaneous, Dual, Stable Isotope Administration: Bioequivalence Implications," *J. Clin. Pharmacol.*, 1999, 39:817-825.

Honma et al., "The Metabolism of Roxatidine Acetate Hydrochloride. Liberation of Deuterium from the Piperidine Ring during Hydroxylation," *Drug Metab. Dispos.*, 1987, 15(4):551-559.

"Patient Information: Intelence® (etravirine)," Tibotec Therapeutics, Nov. 2009, 33 pages.

Authorized officer Lee W. Young, International Search Report/Written Opinion in PCT/US10/27990 mailed Mar. 19, 2010, 11 pages.

Hendrickx, et al. "In Vivo Metabolism and Mass Balance of the Anti-HIV Compound TMC125 in Laboratory Animals and Healthy Volunteers," *AAPS Annual Meet. and Expo* (2006).

INTELENCE™ (entravirine) Highlights of Prescribing Information (2007), 32 pages.

Pharmacologist's Review on NDA 21-567 (Etravirine) *Dept. of Health and Human Services Public Health Service Food & Drug Administration Center for Drug Evaluation and Research*, Application No. 22-187 (2008), 50 pages.

PCT Preliminary Report on Patentability PCT/US2008/011856, mailed Apr. 29, 2010.

PCT International Search Report & Written Opinion PCT/US2008/011856, mailed Jan. 30, 2009.

* cited by examiner

DEUTERATED ETRAVIRINE

CROSS-REFERENCE TO RELATED APPLICATION

This application claims priority under 35 U.S.C. §119 to U.S. Provisional Application 60/980,869, filed Oct. 18, 2007, the entire contents of which are hereby incorporated by reference.

BACKGROUND

Etravirine, also known as 4-(6-amino-5-bromo-2-(4-cyanophenylamino)pyrimidin-4-yloxy)-3,5-dimethylbenzonitrile, inhibits reverse transcriptase by binding at a non-substrate site on the enzyme, different than that for nucleoside analog reverse transcriptase inhibitors (NRTIs) and nucleotide analog reverse transcriptase inhibitors (NtRTIs). Upon binding to the enzyme at a site proximal to the polymerase active site, etravirine can inhibit the movement of protein domains that are needed to carry out the process of DNA synthesis.

Etravirine is currently approved for human immunodeficiency virus (HIV) infection.

Etravirine in human liver microsomes displays good metabolic stability, degrading by 15% over a 2 hour period (Andries, K et al., Antimicrob Agents Chemother, December 2004, 48(12):4680-6). In humans, etravirine is excreted largely intact, with >85% in the feces and <1% in the urine. Metabolism of etravirine in humans proceeds principally through alkyl oxidation to give the mono- and di-hydroxymethyl derivatives which may then undergo glucuronidation. Oxidative enzymes, CYP3A4 and CYP2C19 are largely responsible for the hydroxylation. (Hendrickx, J et al., AAPS J, 2006, 8(suppl 1): Abst M1342).

In trials with HIV-1-infected patients dosed with etravirine, mild side effects included diarrhea, headache, abdominal pain, acute tonsillitis, flatulence, gastroenteritis, hot flushes, insomnia, intercostal pain, pruritus, somnolence, tachycardia and vomiting (Gruzdev, B et al., Interscience Conference on Antimicrobial Agents and Chemotherapy, 2001, 41st:Chicago, 668). In healthy volunteers administered etravirine in combination with lopinavir/ritonavir, the most common adverse effects of the combined regimen were diarrhea and headache (Piscitelli, S C et al., Interscience Conference on Antimicrobial Agents and Chemotherapy, 2002, 42nd:San Diego, Abs A1824). In phase IIb trials with treatment-experienced patients, the safety and tolerability profile of etravirine was generally comparable with placebo (Lazzarin, A et al., Lancet, Jul. 7, 2007, 370(9581):3-5).

Despite the beneficial activities of etravirine, there is a continuing need for new compounds to treat HIV infection.

SUMMARY

This disclosure relates to novel di-aryl-pyrimidine (DAPY) compounds and pharmaceutically acceptable salts thereof. This disclosure also provides compositions comprising a compound of this disclosure and the use of such compositions in methods of treating diseases and conditions that are beneficially treated by administering a non-nucleoside reverse transcriptase inhibitor (NNRTI).

Provided herein is a compound of the Formula I:

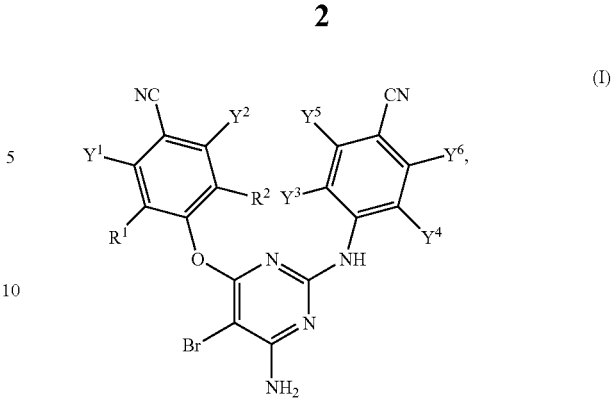

or a pharmaceutically acceptable salt thereof, wherein:
each Y is independently selected from hydrogen and deuterium;
each R is independently selected from —$CH_3$, —$CH_2D$, —$CHD_2$, and —$CD_3$; and
when each R is —$CH_3$, at least one Y is deuterium.

In some embodiments, $Y^1$ and $Y^2$ are the same. In some embodiments, $Y^3$ and $Y^4$ are the same. In some embodiments, $Y^5$ and $Y^6$ are the same. In some embodiments, $R^1$ and $R^2$ are the same. In some embodiments, $R^1$ and $R^2$ are simultaneously —$CH_3$, or —$CD_3$.

In some embodiments, the compound is selected from the group consisting of:

| Compound | $R^1 = R^2$ | $Y^1 = Y^2$ | $Y^3 = Y^4$ | $Y^5 = Y^6$ |
|---|---|---|---|---|
| 100 | $CD_3$ | D | D | D |
| 101 | $CD_3$ | D | D | H |
| 102 | $CD_3$ | D | H | D |
| 103 | $CD_3$ | H | D | D |
| 104 | $CD_3$ | D | H | H |
| 105 | $CD_3$ | H | D | H |
| 106 | $CD_3$ | H | H | D |
| 107 | $CH_3$ | D | D | D |
| 108 | $CH_3$ | D | D | H |
| 109 | $CH_3$ | D | H | D |
| 110 | $CH_3$ | H | D | D |
| 111 | $CH_3$ | D | H | H |
| 112 | $CH_3$ | H | D | H |
| 113 | $CH_3$ | H | H | D |
| 114 | $CD_3$ | H | H | H | or a pharmaceutically acceptable salt thereof.

In some embodiments, any atom not designated as deuterium is present at its natural isotopic abundance.

Also provided is a pyrogen-free pharmaceutical composition comprising a compound of Formula I and a pharmaceutically acceptable carrier. In some embodiments, the composition comprises a second therapeutic agent useful in the treatment of a viral infection. In some embodiments, the second therapeutic agent is useful in the treatment of an HIV infection. In some embodiments, the second therapeutic agent is selected from darunavir, ritonavir, enfuvirtide, tenofovir, emtricitabine, raltegravir, and tipranavir.

Also provided is a method of inhibiting the activity of reverse transcriptase in a virally infected cell, comprising the step of contacting the cell with a compound of Formula I.

In another aspect, a method of treating a patient suffering from or susceptible to a viral infection is provided, comprising the step of administering to the patient in need thereof a composition as described herein. In some embodiments, the patient is suffering from or susceptible to an HIV infection. In some embodiments, the method comprises the additional step of co-administering to the patient in need thereof a second therapeutic agent useful in the treatment of a viral infection. In some embodiments, the second therapeutic agent is useful in the treatment of an HIV infection. In some embodiments, the second therapeutic agent is selected from darunavir, ritonavir, enfuvirtide, tenofovir, emtricitabine, raltegravir, and tipranavir.

DETAILED DESCRIPTION OF THE DISCLOSURE

The terms "ameliorate" and "treat" are used interchangeably and include both therapeutic and/or prophylactic treatment. Both terms mean decrease, suppress, attenuate, diminish, arrest, or stabilize the development or progression of a disease (e.g., a disease or disorder delineated herein), lessen the severity of the disease or improve the symptoms associated with the disease.

"Disease" means any condition or disorder that damages or interferes with the normal function of a cell, tissue, or organ.

It will be recognized that some variation of natural isotopic abundance occurs in a synthesized compound depending upon the origin of chemical materials used in the synthesis. Thus, a preparation of etravirine will inherently contain small amounts of deuterated isotopologues. The concentration of naturally abundant stable hydrogen and carbon isotopes, notwithstanding this variation, is small and immaterial as compared to the degree of stable isotopic substitution of compounds of this disclosure. See, for instance, Wada E et al., Seikagaku 1994, 66:15; Ganes L Z et al., Comp Biochem Physiol Mol Integr Physiol 1998, 119:725. In a compound of this disclosure, when a particular position is designated as having deuterium, it is understood that the abundance of deuterium at that position is substantially greater than the natural abundance of deuterium, which is 0.015%. A position designated as having deuterium typically has a minimum isotopic enrichment factor that is at least 3340 times greater than the natural abundance of deuterium (i.e., the term "D" or "deuterium" indicates at least 50.1% incorporation of deuterium).

The term "isotopic enrichment factor" as used herein means the ratio between the isotopic abundance and the natural abundance of a specified isotope.

In other embodiments, a compound of this disclosure has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium).

The term "isotopologue" refers to a species that has the same chemical structure and formula as a specific compound of this disclosure, with the exception of the positions of isotopic substitution and/or level of isotopic enrichment at one or more positions, e.g., H vs. D.

The term "compound," when referring to a compound of this disclosure, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this disclosure will depend upon a number of factors including the isotopic purity of deuterated reagents used to make the compound and the efficiency of incorporation of deuterium in the various synthesis steps used to prepare the compound. However, as set forth above the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

The disclosure also provides salts of the compounds of the disclosure.

A salt of a compound of this disclosure is formed between an acid and a basic group of the compound, such as an amino functional group, or a base and an acidic group of the compound, such as a carboxyl functional group. According to another embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this disclosure. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The compounds of the present disclosure (e.g., compounds of Formula I), may contain an asymmetric carbon atom, for example, as the result of deuterium substitution or otherwise. As such, compounds of this disclosure can exist as either individual enantiomers, or mixtures of the two enantiomers. Accordingly, a compound of the present disclosure may exist as either a racemic mixture or a scalemic mixture, or as individual respective stereoisomers that are substantially free from another possible stereoisomer. The term "substantially free of other stereoisomers" as used herein means less than 25% of other stereoisomers, preferably less than 10% of other stereoisomers, more preferably less than 5% of other stereoisomers and most preferably less than 2% of other stereoisomers, or less than "X"% of other stereoisomers (wherein X is a number between 0 and 100, inclusive) are present. Methods of obtaining or synthesizing an individual enantiomer for a given compound are known in the art and may be applied as practicable to final compounds or to starting material or intermediates.

Unless otherwise indicated, when a disclosed compound is named or depicted by a structure without specifying the stereochemistry and has one or more chiral centers, it is understood to represent all possible stereoisomers of the compound.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" and "d" both refer to deuterium. "Stereoisomer" refers to both enantiomers and diastereomers. "Tert", "$^t$", and "t-" each refer to tertiary. "US" refers to the United States of America.

Throughout this specification, a variable may be referred to generally (e.g., "each R") or may be referred to specifically (e.g., $R^1$, $R^2$, $R^3$, etc.). Unless otherwise indicated, when a variable is referred to generally, it is meant to include all specific embodiments of that particular variable.

Therapeutic Compounds

The present disclosure provides a compound of Formula I:

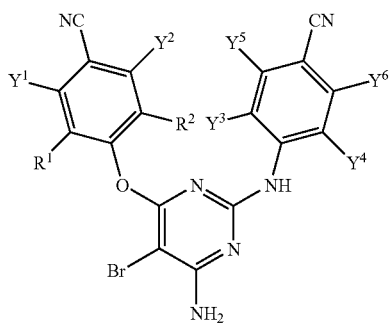

(I)

or a pharmaceutically acceptable salt thereof, wherein:
each Y is independently selected from hydrogen and deuterium;
each R is independently selected from —$CH_3$, —$CH_2D$, —$CHD_2$, and —$CD_3$; and
when each R is —$CH_3$, at least one Y is deuterium.

Other embodiments of the disclosure include a compound of Formula I, wherein
a) $Y^1$ and $Y^2$ are the same;
b) $Y^3$ and $Y^4$ are the same;
c) $Y^5$ and $Y^6$ are the same; or
d) $R^1$ and $R^2$ are the same.

In other embodiments, a compound of Formula I has two or more of the above features a) through d).

In another embodiment, $R^1$ and $R^2$ are simultaneously —$CH_3$, or —$CD_3$. In a more specific embodiment, $R^1$ and $R^2$ are simultaneously —$CH_3$. In another embodiment $R^1$ and $R^2$ are simultaneously —$CD_3$. In various aspects of these embodiments, $Y^1$ is the same as $Y^2$, $Y^3$ is the same as $Y^4$, and/or $Y^5$ is the same as $Y^6$.

Examples of specific compounds of Formula I are shown in Table 1, below.

TABLE 1

Examples of Specific Compounds of Formula I

| Compound | $R^1 = R^2$ | $Y^1 = Y^2$ | $Y^3 = Y^4$ | $Y^5 = Y^6$ |
|---|---|---|---|---|
| 100 | $CD_3$ | D | D | D |
| 101 | $CD_3$ | D | D | H |
| 102 | $CD_3$ | D | H | D |
| 103 | $CD_3$ | H | D | D |
| 104 | $CD_3$ | D | H | H |
| 105 | $CD_3$ | H | D | H |
| 106 | $CD_3$ | H | H | D |
| 107 | $CH_3$ | D | D | D |
| 108 | $CH_3$ | D | D | H |
| 109 | $CH_3$ | D | H | D |
| 110 | $CH_3$ | H | D | D |
| 111 | $CH_3$ | D | H | H |
| 112 | $CH_3$ | H | D | H |
| 113 | $CH_3$ | H | H | D |
| 114 | $CD_3$ | H | H | H |

In another set of embodiments, any atom not designated as deuterium in any of the embodiments set forth above is present at its natural isotopic abundance.

In another set of embodiments, the compounds of Formula I are provided in isolated form; e.g., the compound is not in a cell or organism and the compound is separated from some or all of the components that typically accompany it in nature.

In another set of embodiments, the compound of Formula I is purified, e.g., the compound of Formula I is present at a purity of at least 50.1% by weight (e.g., at least 52.5%, 55%, 60%, 65%, 70%, 75%, 80%, 85%, 90%, 95%, 97%, 98%, 98.5%, 99%, 99.5%, or 99.9%) of the total amount of isotopologues of Formula I present, respectively. Thus, in some embodiments, a composition comprising a compound of Formula I can include a distribution of isotopologues of the compound, provided at least 50.1% of the isotopologues by weight are the recited compound.

In some embodiments, any position in the compound of Formula I designated as having D has a minimum deuterium incorporation of at least 50.1% (e.g., at least 52.5%, at least 60%, at least 67.5%, at least 75%, at least 82.5%, at least 90%, at least 95%, at least 97%, at least 99%, or at least 99.5%) at the designated position(s) of the compound of Formula I. Thus, in some embodiments, a composition comprising a compound of Formula I can include a distribution of isotopologues of the compound, provided at least 50.1% of the isotopologues include a D at the designated position(s).

In some embodiments, a compound of Formula I is "substantially free of" other isotopologues of the compound, e.g., less than 49.9%, less than 25%, less than 10%, less than 5%, less than 2%, less than 1%, or less than 0.5% of other isotopologues are present.

The synthesis of compounds of Formula I can be readily achieved by synthetic chemists of ordinary skill. Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure. Relevant procedures and intermediates are disclosed, for instance in PCT patent publication WO2000/27825; European Patent 1 002 795; U.S. Pat. No. 7,241,458; and Ludovici, D W et al, Biorg Med Chem Lett 2001, 11:2235. The compounds may be prepared as illustrated in the schemes shown below.

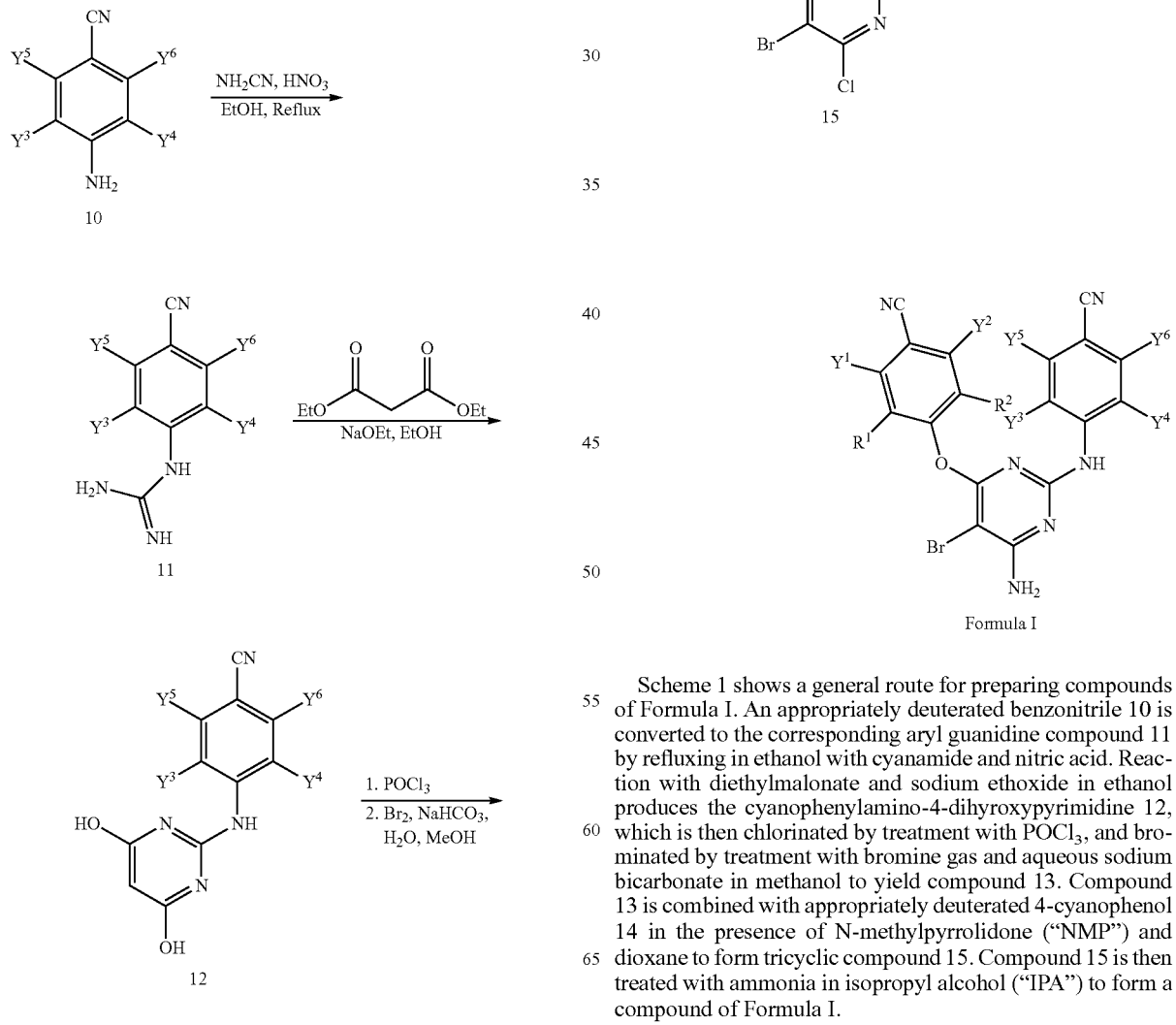

Scheme 1 shows a general route for preparing compounds of Formula I. An appropriately deuterated benzonitrile 10 is converted to the corresponding aryl guanidine compound 11 by refluxing in ethanol with cyanamide and nitric acid. Reaction with diethylmalonate and sodium ethoxide in ethanol produces the cyanophenylamino-4-dihydroxypyrimidine 12, which is then chlorinated by treatment with POCl₃, and brominated by treatment with bromine gas and aqueous sodium bicarbonate in methanol to yield compound 13. Compound 13 is combined with appropriately deuterated 4-cyanophenol 14 in the presence of N-methylpyrrolidone ("NMP") and dioxane to form tricyclic compound 15. Compound 15 is then treated with ammonia in isopropyl alcohol ("IPA") to form a compound of Formula I.

Scheme 2. Routes for Preparing Starting Material 10a

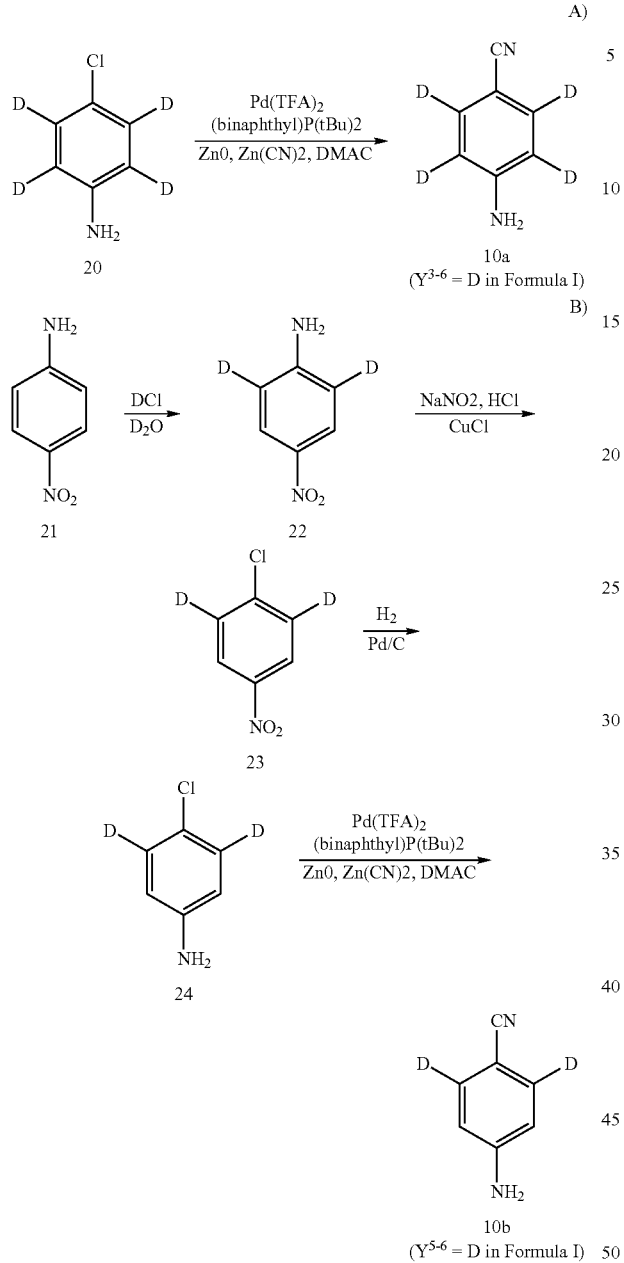

Scheme 3. Routes for Preparing Intermediate 14.

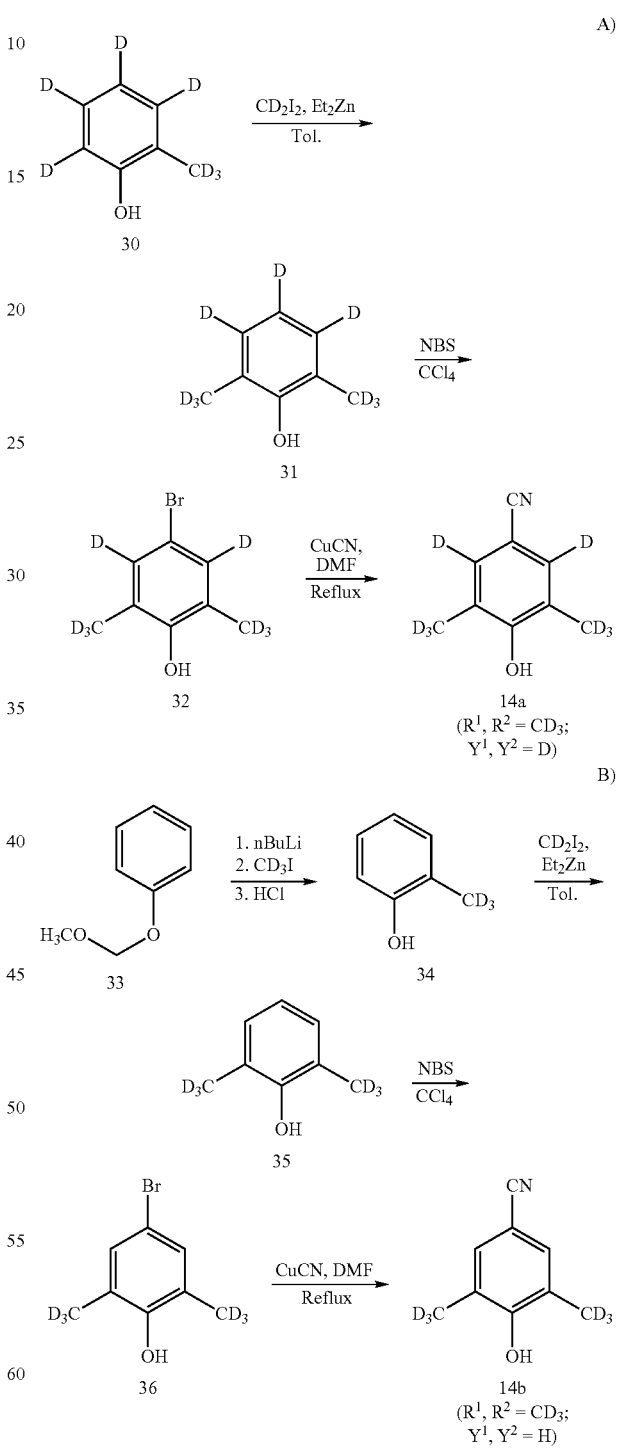

affords the 2,6-$d_2$-4-nitroaniline 22, which can be elaborated through nitrochloro intermediate 23 and chloroaniline intermediate 24 to the necessary $d_2$-benzonitrile building block 10b using the procedures described in Suehiro, T et al., Bull Chem Soc Jap, 1987, 60:3321-3330.

Scheme 2 shows how various deuterated benzonitriles 10, useful in Scheme 1, may be prepared. Reaction A, starting with compound 20, illustrates the preparation of the 4-amino-2,3,5,6-$d_4$-benzonitrile reagent 10a. Treatment of commercially available 4-chloro-2,3,5,6-$d_4$-aniline (20) with palladium(II) trifluoroacetate, 2-di-tert-butylphosphino-1,1'-binaphthyl, zinc flakes, and zinc cyanide according to the procedure described by Littke, A et al., Org Lett, 2007, 9:1711-1714 affords 10a.

Scheme 2B shows the preparation of an alternative benzonitrile intermediate 4-amino-2,6-$d_2$-benzonitrile 10b, starting with commercially available 4-nitroaniline (21). Treatment of 21 with commercially available deuterium chloride in deuterated water according to the procedure described by Suehiro, T et al., Bull Chem Soc Jap, 1987, 60:3321-3330

Scheme 3 shows the synthesis of appropriately deuterated cyanophenols 14 useful in Scheme 1. Sequence A, starting with commercially available ortho-cresol-$d_7$ 30, shows the preparation of the 2,6-$d_2$-4-hydroxy-3,5-bis(methyl-$d_3$)benzonitrile intermediate 14a ($R^1$, $R^2$=$CD_3$; $Y^1$, $Y^2$=D). Treatment of 30 with commercially available $d_2$-diiodomethane and diethylzinc according to the procedure described by Macdonald, T L et al., Tet Lett, 1989, 39:5215-5218 affords the 2,6-bis(methyl-$d_3$)phenol 31. Subsequent bromination of the phenol with N-bromosuccinimde (NBS) in carbon tetrachloride using the protocol described by Srinivasan, K V et al., Tet Lett, 1994, 35:7055-7056 affords the 4-bromo-substituted phenol 32 Treatment of the bromophenol 32 with copper(I) cyanide in refluxing DMF according to the procedure described in Chinese patent publication 1687060 affords the requisite benzonitrile 14a.

Scheme 3B, starting with commercially available 1-(methoxymethoxy)benzene (33), illustrates the preparation of 4-hydroxy-3,5-bis(methyl-$d_3$)benzonitrile 14b ($R^1$, $R^2$=$CD_3$; $Y^1$, $Y^2$=H). Treatment of 33 with n-butyllithium followed by treatment of the in situ generated organolithium with commercially available $d_3$-iodomethane according to the procedure described by Hayes, R N et al., Aus J Chem, 1989, 42:865-874 affords the 2-(methyl-$d_3$)phenol 34, which can then be processed as shown to afford the desired bis (methyl-$d_3$)benzonitrile (14b: $R^1$, $R^2$=$CD_3$; $Y^1$, $Y^2$=H).

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., $R^1$, $R^2$, $Y^1$, etc.) or not. The suitability of a chemical group in a compound structure for use in the synthesis of another compound is within the knowledge of one of ordinary skill in the art. Additional methods of synthesizing compounds of Formula I and their synthetic precursors, including those within routes not explicitly shown in schemes herein, are within the means of chemists of ordinary skill in the art. Methods for optimizing reaction conditions and, if necessary, minimizing competing by-products, are known in the art. In addition to the synthetic references cited herein, reaction schemes and protocols may be determined by the skilled artisan by use of commercially available structure-searchable database software, for instance, SciFinder® (CAS division of the American Chemical Society), STN® (CAS division of the American Chemical Society), CrossFire Beilstein® (Elsevier MDL), or internet search engines such as Google® or keyword databases such as the US Patent and Trademark Office text database.

The methods described herein may also additionally include steps, either before or after the steps described specifically herein, to add or remove suitable protecting groups in order to ultimately allow synthesis of the compounds herein. In addition, various synthetic steps may be performed in an alternate sequence or order to give the desired compounds. Synthetic chemistry transformations and protecting group methodologies (protection and deprotection) useful in synthesizing the applicable compounds are known in the art and include, for example, those described in Larock R, *Comprehensive Organic Transformations*, VCH Publishers (1989); Greene T W et al., *Protective Groups in Organic Synthesis*, 3$^{rd}$ Ed., John Wiley and Sons (1999); Fieser L et al., *Fieser and Fieser's Reagents for Organic Synthesis*, John Wiley and Sons (1994); and Paquette L, ed., *Encyclopedia of Reagents for Organic Synthesis*, John Wiley and Sons (1995) and subsequent editions thereof.

Combinations of substituents and variables envisioned by this disclosure are only those that result in the formation of stable compounds.

Compositions

The disclosure also provides pyrogen-free pharmaceutical compositions comprising an effective amount of a compound of Formula I (e.g., including any of the formulae herein), or a pharmaceutically acceptable salt thereof; and a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present disclosure in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this disclosure optionally formulated with a poloxamer, such as LUTROL™ and PLURONIC™ (BASF Corporation), or block copolymers of ethylene oxide and propylene oxide. See U.S. Pat. No. 7,014,866; and U.S. patent publications 20060094744 and 20060079502.

The pharmaceutical compositions of the disclosure include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present disclosure suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this disclosure may be administered in the form of suppositories for rectal administration. These compositions can be prepared by mixing a compound of this disclosure with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this disclosure may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz J D and Zaffaroni A C, U.S. Pat. No. 6,803,031, assigned to Alexza Molecular Delivery Corporation.

Topical administration of the pharmaceutical compositions of this disclosure is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this disclosure include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this disclosure may also be topically applied to the lower intestinal tract by rectal suppository formulation or in a suitable enema formulation. Topically-transdermal patches and iontophoretic administration are also included in this disclosure.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of this disclosure may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the disclosure provides a method of coating an implantable medical device comprising the step of contacting said device with the coating composition described above. It will be obvious to those skilled in the art that the coating of the device will occur prior to implantation into a mammal.

According to another embodiment, the disclosure provides a method of impregnating an implantable drug release device comprising the step of contacting said drug release device with a compound or composition of this disclosure. Implantable drug release devices include, but are not limited to, biodegradable polymer capsules or bullets, non-degradable, diffusible polymer capsules and biodegradable polymer wafers.

According to another embodiment, the disclosure provides an implantable medical device coated with a compound or a composition comprising a compound of this disclosure, such that said compound is therapeutically active.

According to another embodiment, the disclosure provides an implantable drug release device impregnated with or containing a compound or a composition comprising a compound of this disclosure, such that said compound is released from said device and is therapeutically active.

Where an organ or tissue is accessible because of removal from the patient, such organ or tissue may be bathed in a medium containing a composition of this disclosure, a composition of this disclosure may be painted onto the organ, or a composition of this disclosure may be applied in any other convenient way.

In another embodiment, a composition of this disclosure further comprises a second therapeutic agent. The second therapeutic agent may be selected from any compound or therapeutic agent known to have or that demonstrates advantageous properties when administered with a compound having the same mechanism of action as etravirine. Such agents include those indicated as being useful in combination with etravirine, including but not limited to, those described in WO 2006052373.

Preferably, the second therapeutic agent is an agent useful in the treatment or prevention of a viral infection, more specifically a HIV infection.

In one embodiment, the second therapeutic agent is selected from darunavir, ritonavir, enfuvirtide, tenofovir, emtricitabine, raltegravir, and tipranavir.

In another embodiment, the disclosure provides separate dosage forms of a compound of this disclosure and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the disclosure, the compound of the present disclosure is present in an effective amount. As used herein, the term "effective amount" refers to an amount which, when administered in a proper dosing regimen, is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy.

The interrelationship of dosages for animals and humans (based on milligrams per meter squared of body surface) is described in Freireich et al., (1966) Cancer Chemother. Rep 50: 219. Body surface area may be approximately determined from height and weight of the patient. See, e.g., Scientific Tables, Geigy Pharmaceuticals, Ardsley, N.Y., 1970, 537.

In one embodiment, an effective amount of a compound of this disclosure can range from about 2 mg to about 12,000 mg per treatment. In more specific embodiments the range is from about 20 to 6000 mg, or from about 40 to 2400 mg, or most specifically from about 200 to 1200 mg per treatment. Treatment typically is administered from one to two times daily.

Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician. For example, guidance for selecting an effective dose can be determined by reference to the prescribing information for etravirine.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

It is expected that some of the second therapeutic agents referenced above will act synergistically with the compounds of this disclosure. When this occurs, it will allow the effective dosage of the second therapeutic agent and/or the compound of this disclosure to be reduced from that required in a monotherapy. This has the advantage of minimizing toxic side effects of either the second therapeutic agent of a compound of this disclosure, synergistic improvements in efficacy, improved ease of administration or use and/or reduced overall expense of compound preparation or formulation.

Methods of Treatment

In another embodiment, the disclosure provides a method of blocking the activity of reverse transcriptase in an infected cell, comprising contacting such a cell with one or more compounds of Formula I, or a pharmaceutically acceptable salt thereof.

According to another embodiment, the disclosure provides a method of treating a patient suffering from, or susceptible to, a disease that is beneficially treated by etravirine comprising the step of administering to said patient an effective amount of a compound or a composition of this disclosure. Such diseases are well known in the art and are disclosed in, but not limited to the following patents and published applications: WO 2000027825, WO 2001022938, and WO 2006052373.

In another particular embodiment, the method of this disclosure is used to treat a patient suffering from or susceptible to a viral infection, more specifically a HIV infection.

Methods delineated herein also include those wherein the patient is identified as in need of a particular stated treatment. Identifying a patient in need of such treatment can be in the judgment of a patient or a health care professional and can be subjective (e.g. opinion) or objective (e.g. measurable by a test or diagnostic method).

In another embodiment, any of the above methods of treatment comprises the further step of co-administering to said patient one or more second therapeutic agents. The choice of second therapeutic agent may be made from any second therapeutic agent known to be useful for co-administration with etravirine. The choice of second therapeutic agent is also dependent upon the particular disease or condition to be treated. Examples of second therapeutic agents that may be employed in the methods of this disclosure are those set forth above for use in combination compositions comprising a compound of this disclosure and a second therapeutic agent.

In particular, the combination therapies of this disclosure include co-administering a compound of Formula I and a second therapeutic agent selected from darunavir, ritonavir, enfuvirtide, tenofovir, emtricitabine, raltegravir, and tipranavir for treatment of HIV infection. (See clinical trial information for etravirine at http://clinicaltrials.gov/ct/search;jsessionid=435AE7A09592E6B3155225093E-A21DF1?term=etravirine.

The term "co-administered" as used herein means that the second therapeutic agent may be administered together with a compound of this disclosure as part of a single dosage form (such as a composition of this disclosure comprising a compound of the disclosure and an second therapeutic agent as described above) or as separate, multiple dosage forms. Alternatively, the additional agent may be administered prior to, consecutively with, or following the administration of a compound of this disclosure. In such combination therapy treatment, both the compounds of this disclosure and the second therapeutic agent(s) are administered by conventional methods. The administration of a composition of this disclosure, comprising both a compound of the disclosure and a second therapeutic agent, to a patient does not preclude the separate administration of that same therapeutic agent, any other second therapeutic agent or any compound of this disclosure to said patient at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the disclosure, where a second therapeutic agent is administered to a subject, the effective amount of the compound of this disclosure is less than its effective amount would be where the second therapeutic agent is not administered. In another embodiment, the effective amount of the second therapeutic agent is less than its effective amount would be where the compound of this disclosure is not administered. In this way, undesired side effects associated with high doses of either agent may be minimized. Other potential advantages (including without limitation improved dosing regimens and/or reduced drug cost) will be apparent to those of skill in the art.

In yet another aspect, the disclosure provides the use of a compound of Formula I alone or together with one or more of the above-described second therapeutic agents in the manufacture of a medicament, either as a single composition or as separate dosage forms, for treatment or prevention in a patient of a disease, disorder or symptom set forth above. Another aspect of the disclosure is a compound of Formula I for use in the treatment or prevention in a patient of a disease, disorder or symptom thereof delineated herein.

Diagnostic Methods and Kits

The compounds and compositions of this disclosure are also useful as reagents in methods for determining the concentration of etravirine in solution or biological sample such as plasma, examining the metabolism of etravirine and other analytical studies.

According to one embodiment, the disclosure provides a method of determining the concentration, in a solution or a biological sample, of etravirine, comprising the steps of:
a) adding a known concentration of a compound of Formula I to the solution of biological sample;
b) subjecting the solution or biological sample to a measuring device that distinguishes etravirine from a compound of Formula I;
c) calibrating the measuring device to correlate the detected quantity of the compound of Formula I with the known concentration of the compound of Formula I added to the biological sample or solution; and
d) measuring the quantity of etravirine in the biological sample with said calibrated measuring device; and
e) determining the concentration of etravirine in the solution of sample using the correlation between detected quantity and concentration obtained for a compound of Formula I.

Measuring devices that can distinguish etravirine from the corresponding compound of Formula I include any measuring device that can distinguish between two compounds that differ from one another in isotopic abundance at one or more positions. Exemplary measuring devices include a mass spectrometer, NMR spectrometer, or IR spectrometer.

In another embodiment, the disclosure provides a method of evaluating the metabolic stability of a compound of Formula I comprising the steps of contacting the compound of Formula I with a metabolizing enzyme source for a period of time and comparing the amount of the compound of Formula I with the metabolic products of the compound of Formula I after the period of time.

In a related embodiment, the disclosure provides a method of evaluating the metabolic stability of a compound of Formula I in a patient following administration of the compound of Formula I. This method comprises the steps of obtaining a serum, urine, blood, tissue or feces sample from the patient at a period of time following the administration of the compound of Formula I to the subject; and comparing the amount of the compound of Formula I with the metabolic products of the compound of Formula I in the serum, urine, blood, tissue or feces sample.

The present disclosure also provides kits for use to treat HIV infection, and viral infection. These kits comprise (a) a pharmaceutical composition comprising a compound of Formula I or a salt, thereof, wherein said pharmaceutical composition is in a container; and (b) instructions describing a method of using the pharmaceutical composition to treat HIV infection, and viral infection.

The container may be any vessel or other sealed or sealable apparatus that can hold said pharmaceutical composition. Examples include bottles, ampules, divided or multi-chambered holders bottles, wherein each division or chamber comprises a single dose of said composition, a divided foil packet wherein each division comprises a single dose of said composition, or a dispenser that dispenses single doses of said composition. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box. In one embodiment, the container is a blister pack.

The kits of this disclosure may also comprise a device to administer or to measure out a unit dose of the pharmaceutical composition. Such device may include an inhaler if said composition is an inhalable composition; a syringe and needle if said composition is an injectable composition; a syringe, spoon, pump, or a vessel with or without volume markings if said composition is an oral liquid composition; or any other measuring or delivery device appropriate to the dosage formulation of the composition present in the kit.

In certain embodiment, the kits of this disclosure may comprise in a separate vessel of container a pharmaceutical composition comprising a second therapeutic agent, such as one of those listed above for use for co-administration with a compound of this disclosure.

EXAMPLES

Example 1

Synthesis of 2,6-$d_2$-4-hydroxy-3,5-bis(methyl-$d_3$) benzonitrile (14b)

Intermediate 14b was prepared as outlined in Scheme 4 below. Details of the synthesis follow.

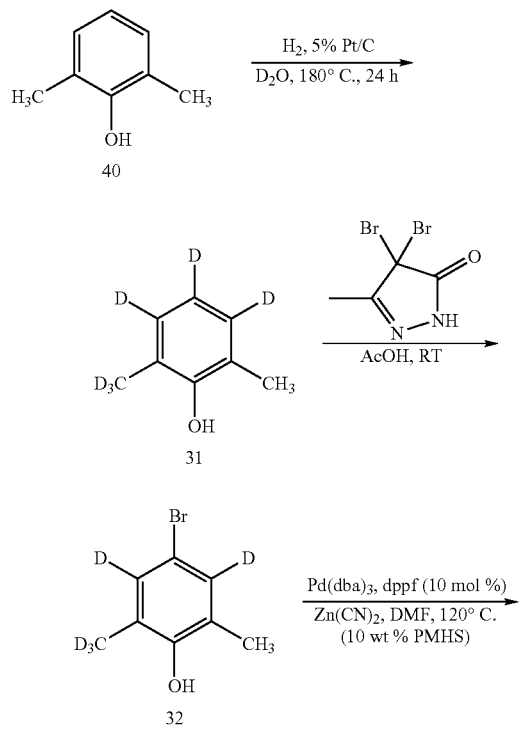

Synthesis of 3,4,5-$d_3$-2,6-bis(methyl-$d_3$)phenol (31). To a sealed tube containing a suspension of 2,6-dimethylphenol 40 (2.0 g, 16.4 mmol) in $D_2O$ (25 mL), was added 5% Pt/C (20 wt %, 0.40 g). The mixture was purged with nitrogen then placed under an $H_2$ atmosphere and stirred at ambient temperature for 15 minutes (min). The tube was then sealed and the mixture heated to 180° C. for a period of 24 hours (h). After cooling to ambient temperature, the mixture was diluted with $Et_2O$ and filtered through Celite. The aqueous phase was extracted with $Et_2O$ (3×25 mL) and the organic extracts were dried, (MgSO$_4$), filtered, and concentrated in vacuo to afford 1.8 g (84%) of pure 31 as a white solid; 98% D incorporation by $^1$H NMR.

Synthesis of 4-bromo-3,5-$d_2$-2,6-bis(methyl-$d_3$)phenol (32). To a solution of 31 (1.6 g, 12.2 mmol) in AcOH (12 mL) at ambient temperature, was added 4,4-dibromo-3-methylpyrazol-5-one (3.1 g, 12.2 mmol, 1.0 equiv). The mixture was stirred at ambient temperature for period of 20 h then filtered through Celite and washed with cold AcOH (5 mL). The mixture was then concentrated in vacuo and the residue obtained was diluted with $H_2O$ (15 mL) and neutralized with a saturated aqueous NaHCO$_3$ solution. The aqueous mixture was then extracted with hexane/$Et_2O$ (1:1, 3×15 mL) and the organic extracts were dried, (MgSO$_4$), filtered, and concentrated in vacuo. Purification of the crude mixture on SiO$_2$ (10%-20% EtOAc/Hex) afforded 1.4 g (79%) of pure 32 as a white solid;

Synthesis of 2,6-$d_2$-4-hydroxy-3,5-bis(methyl-$d_3$)benzonitrile (14b). To a sealed vessel containing a solution of phenol 32 (1.45 g, 6.93 mmol) in DMF (15 mL), was added zinc cyanide (0.98 g, 8.32 mmol, 1.2 equiv), Pd$_2$(dba)$_3$ (0.36 g, 0.35 mmol, 5 mol %), dppf (0.19 g, 0.35 mmol, 5 mol %), polymethylhydrosiloxane (PMHS, 0.15 g, 10 wt %) and water (0.35 mL). The vessel was sealed and heated to 120° C. for a period of 18 h. After cooling to ambient temperature, the mixture was diluted with $H_2O$ (20 mL) and $Et_2O$ (20 mL). The aqueous phase was further extracted with $Et_2O$ (3×20 mL) and the organic extracts were dried, (MgSO$_4$), filtered, and concentrated in vacuo. Purification of the crude mixture on SiO$_2$ (10%-20% EtOAc/Hex) afforded 1.0 g (92%) of pure 14b as an off-white solid.

Example 2

Synthesis of 104

Compound 104 was prepared as outlined in Scheme 5 below. Details of the synthesis follow. Pyrimidine 42 was prepared as set forth in Ludovici, D W et al., Biorg. Med. Chem. Lett. 2001, 11:2235-2239.

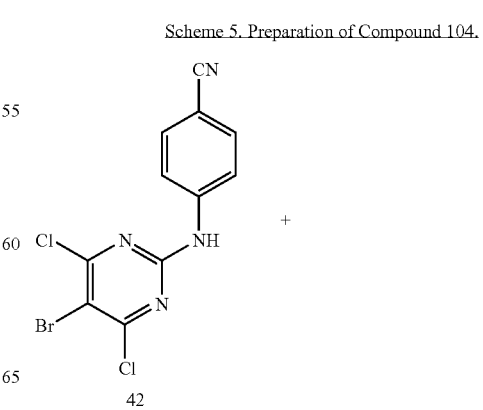

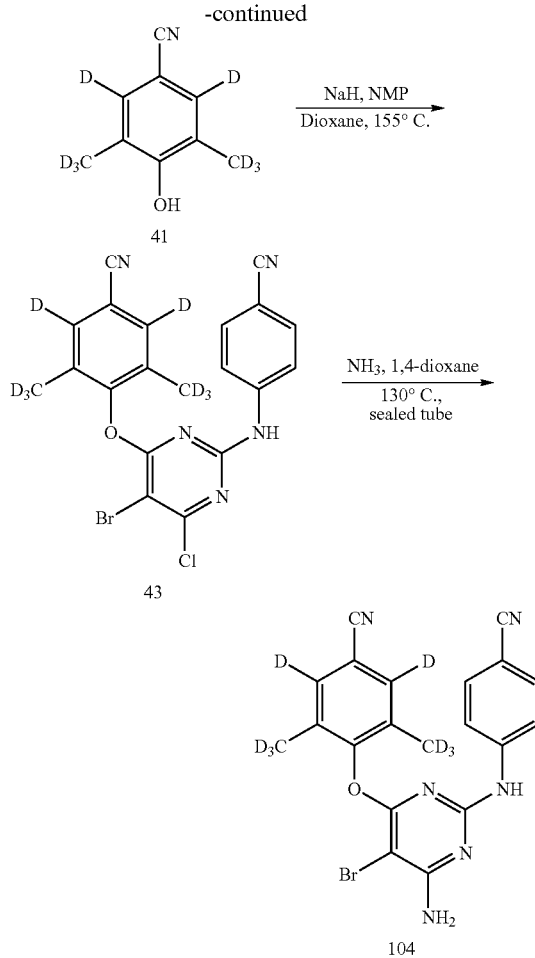

Synthesis of 4-(5-bromo-6-chloro-2-(4-cyanophenylamino)pyrimidin-4-yloxy)-2,6-d$_2$-3,5-bis(methyl-d$_3$)benzonitrile (43). To a sealed tube containing a solution of nitrile 41 (100 mg, 0.64 mmol, 1.1 equiv) in 1,4-dioxane (0.6 mL), was added NaH (26 mg, 0.64 mmol, 1,1 equiv). The mixture was stirred at ambient temperature for a period of 2 min, NMP (0.6 mL) was added, and the resulting mixture was stirred for an additional 10 min at ambient temperature. Pyrimidine 42 (0.20 g, 0.58 mmol, 1.0 equiv) was added to the mixture, and the vessel was sealed and heated to 155° C. for a period of 16 h. After cooling to ambient temperature, the mixture was diluted with H$_2$O (4 mL) and the crude product was filtered off and washed with additional water. Purification of the crude solid on SiO$_2$ (70% CH$_2$Cl$_2$/Hexanes) afforded 72 mg (27%) of pure 43 as a white solid.

Synthesis of 4-(6-amino-5-bromo-2-(4-cyanophenylamino)pyrimidin-4-yloxy)-2,6-dideutero-3,5-bis(trideuteromethyl)benzonitrile (104) Pyrimidine 43 (72 mg, 0.16 mmol) was dissolved in a 0.5 M solution of 1,4-dioxane (4 mL) in a sealed tube. The vessel was heated to 130° C. for a period of 24 h. After cooling to ambient temperature, the mixture was concentrated in vacuo. Purification of the crude mixture on SiO$_2$ (0.25%-0.5% MeOH*/CH$_2$Cl$_2$) (*2.0 M NH$_3$ in MeOH) afforded 12.1 mg (17%) of pure 104 as a white solid. $^1$H NMR (400 MHz, CDCl$_3$): δ 7.39 (d, J=8.8, 2H), 7.30 (d, J=8.8, 2H), 6.82 (br s, 1H), 5.33 (br s, 2H). HPLC (method: 150 mm C18-RP column—gradient method 5-95% ACN; Wavelength: 254 nm): retention time: 5.39 min; purity: 97.8%. MS (M+H): 443.0, 445.1.

Evaluation of Metabolic Stability

Certain in vitro liver metabolism studies have been described previously in the following references, each of which is incorporated herein in their entirety: Obach, R S, Drug Metab Disp, 1999, 27:1350; Houston, J B et al., Drug Metab Rev, 1997, 29:891; Houston, J B, Biochem Pharmacol, 1994, 47:1469; Iwatsubo, T et al., Pharmacol Ther, 1997, 73:147; and Lave, T, et al., Pharm Res, 1997, 14:152.

Microsomal Assay. Human liver microsomes (20 mg/mL) are obtained from Xenotech, LLC (Lenexa, Kans.). β-nicotinamide adenine dinucleotide phosphate, reduced form (NADPH), magnesium chloride (MgCl$_2$), and dimethyl sulfoxide (DMSO) are purchased from Sigma-Aldrich. The incubation mixtures are prepared according to Table 2:

TABLE 2

| Reaction Mixture Composition for Human Liver Microsome Study | |
|---|---|
| Liver Microsomes | 3.0 mg/mL |
| Potassium Phosphate, pH 7.4 | 100 mM |
| Magnesium Chloride | 10 mM |

Determination of Metabolic Stability: Two aliquots of this reaction mixture are used for a compound of this disclosure. The aliquots are incubated in a shaking water bath at 37° C. for 3 minutes. The test compound is then added into each aliquot at a final concentration of 0.5 μM. The reaction is initiated by the addition of cofactor (NADPH) into one aliquot (the other aliquot lacking NADPH serves as the negative control). Both aliquots are then incubated in a shaking water bath at 37° C. Fifty microliters (50 μL) of the incubation mixtures are withdrawn in triplicate from each aliquot at 0, 5, 10, 20, and 30 minutes and combined with 50 μL of ice-cold acetonitrile to terminate the reaction. The same procedure is followed for etravirine and an appropriate positive control. Testing is done in triplicate.

Data analysis: The in vitro half-lives ($t_{1/2}$s) for test compounds are calculated from the slopes of the linear regression of % parent remaining (ln) versus incubation time relationship.

in vitro $t_{1/2}$=0.693/k k=−[slope of linear regression of % parent remaining (ln) vs incubation time]

Data analysis is performed using Microsoft Excel Software.

The metabolic stability of compounds of Formula I is tested using pooled liver microsomal incubations. Full scan LC-MS analysis is then performed to detect major metabolites. Samples of the test compounds, exposed to pooled human liver microsomes, are analyzed using HPLC-MS (or MS/MS) detection. For determining metabolic stability, multiple reaction monitoring (MRM) is used to measure the disappearance of the test compounds. For metabolite detection, Q1 full scans are used as survey scans to detect the major metabolites.

SUPERSOMES™ Assay. Various human cytochrome P450-specific SUPERSOMES™ are purchased from Gentest (Woburn, Mass., USA). A 1.0 mL reaction mixture containing 25 pmole of SUPERSOMES™, 2.0 mM NADPH, 3.0 mM MgCl, and 1 μM of a compound of Formula I in 100 mM potassium phosphate buffer (pH 7.4) is incubated at 37° C. in triplicate. Positive controls contain 1 μM of etravirine instead of a compound of formula I. Negative controls used Control Insect Cell Cytosol (insect cell microsomes that lacked any human metabolic enzyme) purchased from GenTest (Woburn, Mass., USA). Aliquots (50 μL) are removed from each sample and placed in wells of a multi-well plate at various time points (e.g., 0, 2, 5, 7, 12, 20, and 30 minutes) and to each aliquot is added 50 μL of ice cold acetonitrile with 3 μM haloperidol as an internal standard to stop the reaction.

Plates containing the removed aliquots are placed in −20° C. freezer for 15 minutes to cool. After cooling, 100 μL of deionized water is added to all wells in the plate. Plates are then spun in the centrifuge for 10 minutes at 3000 rpm. A portion of the supernatant (100 μL) is then removed, placed in a new plate and analyzed using Mass Spectrometry.

Without further description, it is believed that one of ordinary skill in the art can, using the preceding description and the illustrative examples, make and utilize the compounds of the present disclosure and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the disclosure. All the patents, journal articles and other documents discussed or cited above are herein incorporated by reference.

I claim:

1. A compound of the Formula I:

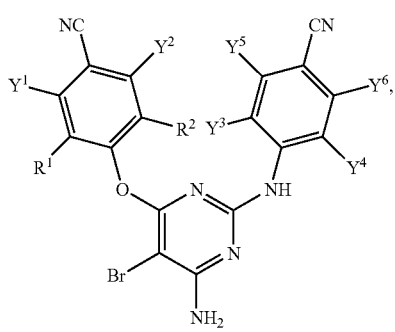

(I)

or a pharmaceutically acceptable salt thereof, wherein:
$Y^1$ and $Y^2$ are the same and are selected from hydrogen and deuterium;
$Y^3$, $Y^4$, $Y^5$, and $Y^6$ are independently selected from hydrogen and deuterium; and
each R is —$CD_3$.

2. The compound of claim 1, wherein $Y^3$ and $Y^4$ are the same.

3. The compound of claim 1, wherein $Y^5$ and $Y^6$ are the same.

4. The compound of claim 1, selected from the group consisting of:

| Compound | $R^1 = R^2$ | $Y^1 = Y^2$ | $Y^3 = Y^4$ | $Y^5 = Y^6$ |
|---|---|---|---|---|
| 100 | $CD_3$ | D | D | D |
| 101 | $CD_3$ | D | D | H |
| 102 | $CD_3$ | D | H | D |
| 103 | $CD_3$ | H | D | D |
| 104 | $CD_3$ | D | H | H |
| 105 | $CD_3$ | H | D | H |
| 106 | $CD_3$ | H | H | D |
| 114 | $CD_3$ | H | H | H | or a pharmaceutically acceptable salt thereof.

5. The compound of claim 1, wherein any atom not designated as deuterium is present at its natural isotopic abundance.

6. A pyrogen-free pharmaceutical composition comprising a compound of claim 1 and a pharmaceutically acceptable carrier.

7. The composition of claim 6 further comprising a second therapeutic agent useful in the treatment of a viral infection.

8. The composition of claim 7, wherein the second therapeutic agent is useful in the treatment of a HIV infection.

9. The composition of claim 8, wherein the second therapeutic agent is selected from darunavir, ritonavir, enfuvirtide, tenofovir, emtricitabine, raltegravir, and tipranavir.

10. A method of inhibiting the activity of reverse transcriptase in a virally infected cell, comprising the step of contacting the cell with a compound of claim 1.

11. A method of treating a patient suffering from or susceptible to a viral infection comprising the step of administering to the patient in need thereof a composition of claim 6.

12. The method of claim 11, wherein the patient is suffering from or susceptible to an HIV infection.

13. The method of claim 12 comprising the additional step of co-administering to the patient in need thereof a second therapeutic agent useful in the treatment of a viral infection.

14. The method of claim 13, wherein the second therapeutic agent is useful in the treatment of a HIV infection.

15. The method of claim 14, wherein the second therapeutic agent is selected from darunavir, ritonavir, enfuvirtide, tenofovir, emtricitabine, raltegravir, and tipranavir.

* * * * *